United States Patent
Rakow et al.

(10) Patent No.: US 9,291,484 B2
(45) Date of Patent: Mar. 22, 2016

(54) METHOD FOR CORRELATING A MONITORING DEVICE TO THE END OF SERVICE LIFE OF A FILTER CARTRIDGE

(75) Inventors: Neal A. Rakow, Woodbury, MN (US); Stefan H. Gryska, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 136 days.

(21) Appl. No.: 13/876,402

(22) PCT Filed: Aug. 31, 2011

(86) PCT No.: PCT/US2011/049828
§ 371 (c)(1),
(2), (4) Date: Jun. 24, 2013

(87) PCT Pub. No.: WO2012/044430
PCT Pub. Date: Apr. 5, 2012

(65) Prior Publication Data
US 2013/0263640 A1 Oct. 10, 2013

Related U.S. Application Data

(60) Provisional application No. 61/388,659, filed on Oct. 1, 2010.

(51) Int. Cl.
| | |
|---|---|
| *B01D 53/02* | (2006.01) |
| *G01N 21/29* | (2006.01) |
| *G01D 18/00* | (2006.01) |
| *A62B 18/08* | (2006.01) |
| *B01D 53/04* | (2006.01) |
| *G01N 33/00* | (2006.01) |
| *G01F 25/00* | (2006.01) |
| *B01D 53/72* | (2006.01) |
| *G01N 21/78* | (2006.01) |

(52) U.S. Cl.
CPC ............. *G01D 18/00* (2013.01); *A62B 18/088* (2013.01); *B01D 53/0454* (2013.01); *G01F 25/00* (2013.01); *G01N 33/007* (2013.01); *B01D 53/72* (2013.01); *B01D 2253/102* (2013.01); *B01D 2253/104* (2013.01); *B01D 2253/106* (2013.01); *B01D 2253/116* (2013.01); *B01D 2253/1124* (2013.01); *B01D 2253/204* (2013.01); *B01D 2257/708* (2013.01); *B01D 2257/7022* (2013.01); *B01D 2257/7027* (2013.01); *B01D 2258/06* (2013.01); *B01D 2259/4541* (2013.01); *G01N 21/783* (2013.01)

(58) Field of Classification Search
CPC .......... B01D 46/0086; B01D 46/2411; B01D 46/46; B01D 53/0415; B01D 53/0454; B01D 53/72; B01D 2253/102; B01D 2253/104; B01D 2253/106; B01D 2253/1124; B01D 2253/116; B01D 2253/204; B01D 2257/7022; B01D 2257/7027; B01D 2257/708; B01D 2258/06; B01D 2259/4541; A62B 18/088; A62B 9/006; G01N 27/78; G01D 18/00; G01F 25/00
USPC ........................ 95/90, 141, 143; 73/1.01, 1.16
See application file for complete search history.

(56) References Cited

U.S. PATENT DOCUMENTS

| | | |
|---|---|---|
| 3,971,373 A | 7/1976 | Braun |
| 4,135,896 A | 1/1979 | Parish |
| 4,208,194 A | 6/1980 | Nelson |
| 4,237,726 A | 12/1980 | Peterson |
| 4,326,514 A | 4/1982 | Eian |
| 4,421,719 A | 12/1983 | Burleigh |
| 4,552,570 A | 11/1985 | Gravatt |
| 4,948,639 A | 8/1990 | Brooker |
| 5,858,457 A | 1/1999 | Brinker |
| 5,976,467 A | 11/1999 | Dallas |
| 6,187,596 B1 | 2/2001 | Dallas |
| 6,312,793 B1 | 11/2001 | Grill |
| 6,497,756 B1 | 12/2002 | Curado |
| 6,573,305 B1 | 6/2003 | Thunhorst |
| 7,201,036 B2 | 4/2007 | Custer |
| 7,442,237 B1 * | 10/2008 | Gardner ...................... 96/117.5 |
| 7,449,146 B2 | 11/2008 | Rakow |
| 2004/0184948 A1 | 9/2004 | Rakow |

| 2005/0217486 A1* | 10/2005 | Robinson et al. ............... 96/118 |
|---|---|---|
| 2006/0096911 A1 | 5/2006 | Brey |
| 2007/0141580 A1 | 6/2007 | David |
| 2007/0277592 A1 | 12/2007 | Johansson |
| 2008/0063574 A1 | 3/2008 | Centanni |
| 2008/0063575 A1 | 3/2008 | Rakow |
| 2008/0063874 A1 | 3/2008 | Rakow |
| 2008/0210084 A1* | 9/2008 | Ota et al. ............................ 95/11 |
| 2009/0007790 A1* | 1/2009 | Mochizuki ....................... 96/153 |
| 2009/0056536 A1* | 3/2009 | Wright ............................... 95/25 |
| 2009/0192037 A1* | 7/2009 | Bohringer et al. ............ 502/403 |
| 2010/0006505 A1 | 1/2010 | Smith |
| 2011/0094514 A1 | 4/2011 | Rackow |

FOREIGN PATENT DOCUMENTS

| JP | H01-156730 | 10/1989 |
|---|---|---|
| WO | WO 2005-012397 | 2/2005 |
| WO | WO 2007-075273 | 7/2007 |
| WO | WO 2010-117599 | 10/2010 |
| WO | WO 2011-123403 | 10/2011 |
| WO | WO 2012-044430 | 4/2012 |

OTHER PUBLICATIONS

Davankov, "Structure and properties of porous hypercrosslinked polystyrene sorbents Styrosorb", Pure and Appl. Chem., 1989, vol. 61, No. 11, pp. 1881-1889.

Belyakova, "Sorption of vapors of various substances by hupercrosslinked styrosorb polystyrenes", Adv. in Colloid and Interface Sci., 1986, vol. 25, pp. 249-266.

Krause, "Bicontinuous Nanoporous Polymers by Carbon Dioxide Foaming", Macromolecules, Nov. 1, 2001, vol. 34, No. 25, pp. 8792-8801.

Walheim, "Nanophase-Separated Polymer Films as High-Performance Antireflection Coatings", Science, 1999, vol. 283, No. 5401, pp. 520-522.

Ogawa, "A Simple sol-gel route for the preparation of silica-surfactant mesostructured materials", Chem. Commun., 1996, pp. 1149-1150.

Kresge, "Ordered mesoporous molecular sieves sunthesized by a liqid-crystal template meachanism", Nature, 1992, vol. 359, pp. 710-712.

Jia, "Synthesis of Microporous Silica Templated by Gelatin", Chemistry Letters, 2004, vol. 33, No. 2, pp. 202-203.

Wei, "A Non-surfactant Templating Route to Mesoporous Silica Materials", Adv. Mater., 1998, vol. 10, No. 4, pp. 313-316.

Budd, "Polymers of intrinsic microporosity (PIMs): robust, solution-processable, organic microporous materials," Chem. Commun., 2004, pp. 230-231.

Budd, "Free volume and intrinsic microporosity in polymers", J. Mater. Chem., 2005, vol. 15, pp. 1977-1986.

McKeown, "Polymers of Intrinsic Microporosity (PIMs): Bridging the Void between Microporous and Polymeric Materials," Chem. Eur. J., 2005, vol. 11, No. 9, pp. 2610-2620.

Cohen, "Development of a Field Method for Evaluating the Service Life of Organic Vapor Cartridges: Results of Laboratory Testing Using Carbon Tetrachloride", Am. Ind. Assoc. J., 1989, vol. 50, No. 9, 486-495.

Wood, "Estimating Service Lives of Organic Vapor Cartridges", Am. Ind. Hyg. Assn. J., 1994, vol. 55, No. 1, pp. 11-15.

International Search Report for PCT/US2011/049828, mailed on Apr. 9, 2012, 3 pages.

* cited by examiner

*Primary Examiner* — Frank Lawrence
(74) *Attorney, Agent, or Firm* — Jeffrey M. Olofson

(57) ABSTRACT

Methods of correlating a monitoring device to the service life of a filter cartridge include providing a monitoring device, and calibrating the monitoring device to correspond to the service life of a filter cartridge. The monitoring device comprises a demand substance within a receptacle, a sensing element with a detection point, a reader for the sensing element, and a fluid delivery device. Calibration includes determining the ratio of the residence time of the monitoring device to the residence time of the filter cartridge, and utilizing the ratio to correlate the response of the sensor within the monitoring device to the service life of the filter cartridge. The response of the sensor is correlated to the service life of the filter cartridge by control of the fluid delivery parameters of the fluid delivery device. The fluid delivery parameters include the flow rate, the demand substance mass, the receptacle cross sectional area, the receptacle volume, the receptacle length, and the demand substance packing density.

20 Claims, 4 Drawing Sheets

METHOD FOR CORRELATING A MONITORING DEVICE TO THE END OF SERVICE LIFE OF A FILTER CARTRIDGE

FIELD OF THE DISCLOSURE

The present disclosure relates to methods for using monitors to indicate the end of useful service life of air purification systems.

BACKGROUND

A variety of air purification systems have been developed to protect people from hazardous air contaminants. Among these air purification systems are a wide range of air purifying respirators that are designed to filter out or sorb contaminants present in the air. Typically these air purifying respirators contain a filter media, a filter body, or some combination of filter media and filter body. Upon use of the respirator, the contaminants become absorbed by the filter media or attached or trapped by the filter body. Eventually, the filter media or filter body becomes saturated and the ability of the respirator to remove the hazardous air contaminants begins to diminish.

During extended exposure to an environment containing hazardous air contaminants, such as, for example, continuous or repeated worker exposure to such environments, techniques are necessary to determine the useful service life of a respirator. One technique that has been developed is based upon the time in service for a respirator. In this technique, respirators or the air purifying filters are replaced after a certain period of time in service. However, this technique does not take into account variations in contaminant level or flow rates through the respirator and therefore may result in the respirator or filter elements being changed too early (which is wasteful) or too late (which may present a danger to the user).

SUMMARY

Disclosed herein are methods of correlating a monitoring device to the service life of a filter cartridge. These methods comprise providing a monitoring device, and calibrating the monitoring device to correspond to the service life of a filter cartridge. The monitoring device comprises a demand substance within a receptacle, a sensing element with a detection point, a reader for the sensing element, and a fluid delivery device. The fluid delivery device comprises fluid delivery parameters, wherein the fluid delivery parameters and the detection point of the sensing element are correlated to the service life of a filter cartridge.

Calibrating the monitoring device to correspond to the service life of a filter cartridge comprises determining a residence time for the filter cartridge, determining a residence time for the monitoring device, determining the ratio of the residence time of the monitoring device to the residence time of the filter cartridge, and utilizing the ratio to correlate the response of the sensor within the monitoring device to the service life of the filter cartridge. The response of the sensor within the monitoring device is correlated to the service life of the filter cartridge by control of the fluid delivery parameters of the fluid delivery device. The fluid delivery parameters minimally comprise the flow rate, the demand substance mass, the receptacle cross sectional area, the receptacle volume, the receptacle length, and the demand substance packing density of the monitoring device.

BRIEF DESCRIPTION OF THE DRAWINGS

The disclosure may be more completely understood in consideration of the following detailed description of various embodiments of the disclosure in connection with the accompanying drawings.

Figure 1:
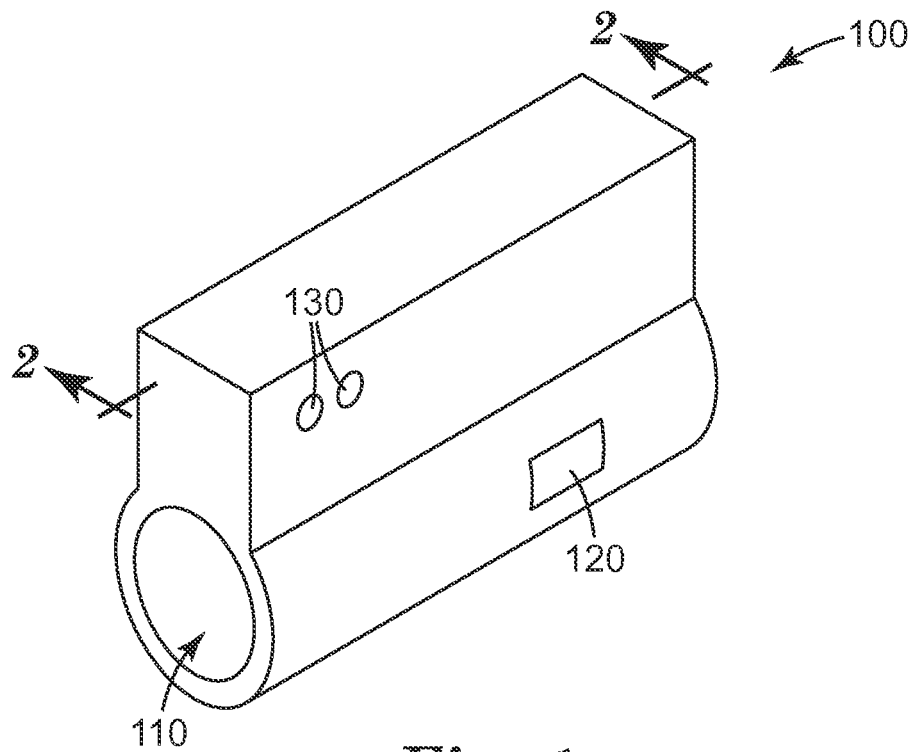
FIG. 1 shows a perspective view of a portable monitor of this disclosure.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present disclosure. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

A need exists for methods and devices to monitor and detect the end of the useful service life of air purification systems such as air purifying respirators. Such devices, sometimes called End of Service Life Indicators or ESLI, should be sufficiently robust to be used in a variety of environments and sufficiently portable to be able to move from location to location with the user of the device and should utilize methods for correlating the end of the useful service life of air purification systems.

Portable devices for monitoring and detecting the end of the useful service life of air purification systems are used in the methods disclosed herein. These portable devices are particularly suitable for monitoring and detecting the end of useful service life of respirators designed to protect against exposure to organic vapors. The term "organic vapor" as used herein, refers to a wide range of volatile airborne organic compounds that may be hazardous to people if present in the air they breathe. Examples of organic vapors include, but are not limited to: alcohols such as isopropanol and butanol; alkanes such as hexane, and octane; aromatics such as benzene, toluene, xylenes, and styrene; halocarbons such as chloroform, and methylene chloride; ketones such as acetone, and methyl ethyl ketone; ethers such as tetrahydrofuran; esters such as ethyl acetate, and ethoxyethyl acetate; acrylates such as methylacrylate; nitriles such as acetonitrile; isocyanates such as toluene-2,4-diisocyanate; and the like. Typically, organic vapor respirators include an absorbent media to trap and hold the organic vapors.

The method for correlating a monitoring device to the useful service life of a filter cartridge comprises providing a monitoring device and calibrating the service life of the monitoring device to correspond to the service life of a filter cartridge. Suitable monitoring devices are described below. The monitoring device mimics the filter cartridge, but is able to be monitored to determine when the useful service life of the filter cartridge has ended. By monitoring the monitoring device and correlating the sensor response of the monitoring device to the end of service life of the filter cartridge, a user is able to determine the useful service life of a filter cartridge.

The correlation of the monitoring device to the end of service life of a filter cartridge is determined by calibrating the monitoring device to the end of service life of a filter cartridge. This calibration is similar to the method used in previous studies by H. J. Cohen and coworkers in the journal reference *Am. Ind. Assoc. J.;* 486-495 (1989), where respirator carbon tubes, or RCTs, were used to predict service life for respirator cartridges. Such devices require large equipment, such as benchtop-scale infrared spectrometer to measure the presence of organic vapors in the output stream of the RCT. While the devices described by Cohen and coworkers are unsuitable for use with the present handheld devices, the calibration method is similar.

This calibration is effected by determining the residence time of the filter cartridge, determining the residence time of the monitoring device and determining the ratio of the residence time of the filter cartridge and the residence time of the monitoring device. The term "residence time" as used herein refers to the time required by a molecule or parcel of air traversing a filtration media to fully traverse that media. The residence time can be controlled by controlling a variety of fluid delivery parameters. Some of these fluid delivery parameters are established by controlling the size of the receptacle containing the filter media. These parameters include the cross sectional area of the receptacle, the receptacle volume, and the receptacle length. Other of these fluid delivery parameters are controlled by the selection of the filter media and the method that the filter media is placed in the receptacle. These parameters include the mass of the filter media and the packing density of the filter media. Still other fluid parameters are controlled by the user of the device, such as the flow rate. Residence time within a respirator cartridge is largely determined by the breathing rate of the user.

Typically, the filter media comprises a demand substance. As used herein, the term "demand substance" refers to a substance capable of absorbing an organic vapor. In some embodiments, it is desirable that the demand substance of the monitoring device be the same as the demand substance of the filter cartridge. In other embodiments, the demand substance of the monitoring device is different from the demand substance of the filter cartridge. Suitable demand substances are described below.

The monitoring device further comprises a sensing element with a detection point, a reader for the sensing element, and a fluid delivery device where the fluid delivery device comprises fluid delivery parameters as described above. Each of these elements of the monitoring device are described in detail below. A monitoring device could be constructed in which the receptacle of the monitoring device is an exact replica of the filter cartridge that it is designed to mimic. For example, the receptacle of the monitoring device could be a filter cartridge identical to the filter cartridge worn by the user. In this case, if the flow rate of the monitor is set to be the same as the flow rate of the filter cartridge, the ratio of residence times of the monitoring device and the filter cartridge is 1:1. While such devices are within the scope of this disclosure, typically the receptacle of the monitoring device is smaller and more portable than the filter cartridge that it is designed to mimic. Additionally, the use of an actual filter cartridge as the receptacle for the monitoring device can be much more expensive than using a smaller and cheaper receptacle.

As described above, correlation of the monitoring device to the end of service life of the filter cartridge is determined by calibrating the monitoring device to the end of service life of a filter cartridge. The calibration is effected by determining the residence time of the filter cartridge, determining the residence time of the monitoring device and determining the ratio of the residence time of the filter cartridge and the residence time of the monitoring device. In some embodiments this ratio is determined to be 1:1. In other embodiments, it may be desirable for this ratio to be less than 1:1. If the ratio is 1:1, the end of service life for the monitor and the filter cartridge are the same. When the ratio is less than 1:1, the end of service life for the monitor will be sooner than the end of service life of the filter cartridge, providing a margin of safety for the user to vacate the hazardous environment before the filter cartridge end of service life.

An additional technique for providing a margin of safety for the user, in embodiments where the sensing element is located within receptacle containing the demand substance, is determined by the location of the sensing element. If the sensing element is located farther upstream within the receptacle, the sensing element is exposed to the organic analyte sooner than the end of service life of the respirator cartridge. Calibration of the location of the sensing element to the end of service life of the filter cartridge can be done mathematically to determine the safety margin, i.e. the time left before the end of service life of the respirator cartridge when a response is detected in the sensing element of the monitoring device. For example, the sensing element can be located at a position such that detection of a sensing element response corresponds to 20 minutes of service life remaining in the respirator cartridge.

The monitoring device may additionally contain more than one sensing element. If more than one sensing element is included, more than just the service life of the monitoring device can be detected. For example, if two sensing elements are used, one can be placed at one at the end of the receptacle containing the demand substance, and the other could be placed at a point before the end of the receptacle containing the demand substance. In this way when the detection point of the sensing element before the end of the receptacle is detected, the user would receive an additional indication that the end of service life of the filter cartridge is approaching. In the same way, a series of sensing elements can be used to provide an array of indications of the approaching end of service life of the filter cartridge.

Determination of the residence time for a given filter cartridge is determined by the fluid delivery parameters of the filter cartridge, namely the dimensions of the cartridge, the packing density and mass of the demand substance, and the flow rate through the filter cartridge. To develop a monitoring device to mimic the working of this filter cartridge, all of the fluid delivery parameters of the monitoring device can be controlled to control the residence time of the monitoring device. Residence times can be determined experimentally or can be calculated or estimated mathematically. For example, in some embodiments it may be desirable to develop a receptacle with the same demand substance and demand substance packing density as the filter cartridge, but receptacle dimensions that are much smaller than the dimensions of the filter cartridge. The receptacle dimensions can be controlled in a variety of different ways. For example, the cross sectional area of the receptacle may be one tenth that of the filter cartridge, but the receptacle length may be the same as the filter cartridge. For such a monitoring receptacle, a flow rate of ten times the flow rate of the filter cartridge can provide a ratio of the residence times of the monitor to the filter cartridge of about 1:1.

In embodiments in which the same demand substance is used and the packing density of the demand substance is similar or the same, a simple alternative method for correlating the monitoring device to the end of service life of the filter cartridge is described by Equation 1 below:

$$t_{SL} = t_b (W_{cartridge} Q_{monitor} / W_{monitor} Q_{cartridge})$$  Equation 1

In Equation 1, $t_{SL}$ is the service life time of the filter cartridge, $t_b$ is the service life time of the monitor, $W_{cartridge}$ is the weight of demand substance in the cartridge, $Q_{monitor}$ is the flow rate in the monitor, $W_{monitor}$ is the weight of demand substance in the monitor, and $Q_{cartridge}$ is the flow rate in the cartridge. The term $t_b$ can be described as the "breakthrough time" for the monitor, or the point at which the demand substance is saturated. Typically, $t_b$ is thus the detection point of the monitor. In other words, when the demand substance is saturated and organic vapors are therefore able to pass through the demand substance and the sensing element is triggered. Presuming that the $W_{cartridge}$ and $Q_{cartridge}$ are known for a given cartridge of interest, $Q_{monitor}$ and $W_{monitor}$ can be controlled to give the desired correlation of $t_b$ to $t_{SL}$.

A wide variety of portable monitoring devices can be used with the methods of this disclosure. Typically, the portable monitoring devices comprise a demand substance, a sensing element with a detection point, a reader for the sensing element, and a fluid delivery device. The sensing element is located within or adjacent to the demand substance. The portable device is correlated such that the detection point of the sensing element corresponds to the service life of a filter cartridge. In some embodiments, detection point comprises an optical change, such as, for example, a color change. In some embodiments, the portable device includes a receptacle which contains at least the demand substance, and may also contain the sensing element.

A wide variety of materials may be suitable for use as the demand substance. As used herein, the term "demand substance" refers to a substance capable of absorbing an organic vapor. In some embodiments, the demand substance comprises a sorbent material. In other embodiments, the demand substance comprises a layered film. In still other embodiments, the demand substance may be granular or monolithic.

In embodiments in which the demand substance comprises a sorbent material, the sorbent material typically is capable of absorbing or adsorbing organic vapors. The sorbent material may be the same, or similar to, the sorbent materials used in filter cartridges of organic vapor respirators. Examples of suitable sorbent materials include, for example, activated carbon, treated activated carbon, alumina, silica gel, hopcalite, molecular sieves, metal-organic frameworks, or a combination thereof.

The disclosed devices may employ a variety of sorbent media. The sorbent media will be capable of sorbing vapors of interest expected to be present under the intended use conditions. The sorbent media desirably is sufficiently porous to permit the ready flow of air or other gases therethrough, and may be in the form of a finely-divided solid (e.g., powder, beads, flakes, granules or agglomerates) or porous solid (e.g., an open-celled foam or a porous monolithic material). Especially desirable sorbent media materials include activated carbon; alumina and other metal oxides that can remove a vapor of interest by adsorption; clay and other minerals treated with acidic solutions such as acetic acid or alkaline solutions such as aqueous sodium hydroxide; molecular sieves and other zeolites; other inorganic sorbents such as silica; and organic sorbents including hypercrosslinked systems, such as the highly crosslinked styrenic polymers known as "Styrosorbs" (as described, for example, in V. A. Davankov and P. Tsyurupa, *Pure and Appl. Chem.*, vol. 61, pp. 1881-89 (1989) and in L. D. Belyakova, T. I. Schevchenko, V. A. Davankov and M. P. Tsyurupa, *Adv. in Colloid and Interface Sci.* vol. 25, pp. 249-66, (1986)). Activated carbon and alumina are particularly desirable sorbent media. Mixtures of sorbent media can be employed, e.g., to absorb mixtures of vapors of interest. If in a finely divided form, the sorbent particle size can vary a great deal and usually will be chosen based in part on the intended service conditions. As a general guide, finely-divided sorbent media particles may vary in size from about 4 to about 5000 micrometers average diameter, e.g., from about 30 to about 1500 micrometers average diameter. Mixtures of sorbent media particles having different size ranges can also be employed, (e.g., in a bimodal mixture of sorbent media particles or in a multilayer arrangement employing larger sorbent particles in an upstream layer and smaller sorbent particles in a downstream layer). Sorbent media combined with a suitable binder (e.g., bonded carbon) or captured on or in a suitable support such as described in U.S. Pat. No. 3,971,373 (Braun et al.), U.S. Pat. No. 4,208,194 (Nelson) and U.S. Pat. No. 4,948,639 (Brooker et al.) and in U.S. Patent Application Publication No. US 2006/0096911 A1 (Brey et al.) may also be employed.

A wide variety of sensing elements are suitable for use in the devices of this disclosure. In some embodiments, the sensing element is located within the same receptacle as the demand substance. In other embodiments, the sensing element is not located within the receptacle, but the stream exiting the demand substance is impinged upon the sensing element.

The sensing element is optically responsive to an analyte, for example, by undergoing a change in at least one of its optical properties (as may be manifested by a colorimetric change, a change in brightness, intensity of reflected light, etc.) when the demand substance becomes equilibrated with the analyte at the conditions of exposure.

The choice of sensing element or sensing elements will depend upon the a variety of criteria, including the nature of reader for the sensing element that is used. If the reader is to be the unaided human eye, the sensing element should display an easily distinguishable optical change. If, however, an electronic reader is utilized, more complex or subtle optical changes are suitable.

In some embodiments the sensing element is a film. The film may have multiple layers and may be a colorimetric film (i.e. the film changes color upon exposure to an organic analyte), or may undergo some other detectable optical change upon exposure to an organic analyte. Examples of suitable sensor films are described in U.S. Pat. No. 7,449,146 (Rakow et al.) and US Patent Publication Nos. 2008/0063575 and 2008/0063874 (Rakow et al.).

When the sensing element is a multi-layer film construction, it typically contains a porous detection layer, a semi-reflective layer, and a reflective layer. The porous detection layer has an optical thickness that will change in the presence of a particular chemical analyte. The semi-reflective layer is viewable from the outside and is generally not permeated by the analyte vapor. The reflective layer is generally permeable to the analyte vapor such that the chemical analyte can pass through the reflective layer into the detection layer and change the detection layer optical thickness sufficiently to cause a visibly discernible change in the sensing element appearance as viewed through the semi-reflective layer.

The reflective layer may, for example, have a physical thickness of about 1 to about 500 nm, light transmission at 500 nm of about 0 to about 80%, and reflectance at 500 nm of about 100 to about 20%. The reflective layer generally is porous, patterned, discontinuous, semi-continuous, or otherwise sufficiently permeable so that vapor can pass from the sorbent media through the reflective layer into the detection layer.

The detection layer mixture may be homogeneous or heterogeneous, and may, for example, be made from a mixture of inorganic components, a mixture of organic components, or a mixture of inorganic and organic components. Detection layers made from a mixture of components may provide improved detection of groups of analytes. The detection layer desirably has a range of pore sizes or a surface area selected to provide vapor sorption characteristics like those of the sorbent media. Suitable porosity can be obtained by using porous materials such as foams made from high internal phase emulsions, such as those described in U.S. Pat. No. 6,573,305 B1 (Thunhorst et al.). Porosity may also be obtained via carbon dioxide foaming to create a microporous material (see "Macromolecules", 2001, vol. 34, pp. 8792-8801), or by nanophase separation of polymer blends (see "Science", 1999, vol. 283, p. 520). In general, the pore diameters preferably are smaller than the peak wavelength of the desired indicator coloration. Nano-sized pores are preferred, e.g., with average pore sizes of about 0.5 to about 20 nm, 0.5 to about 10 nm, or 0.5 to about 5 nm.

Representative inorganic detection layer materials include porous silica, metal oxides, metal nitrides, metal oxynitrides and other inorganic materials that can be formed into transparent and porous layers of appropriate thickness for producing color or a colorimetric change by optical interference. For example, the inorganic detection layer materials may be silicon oxides, silicon nitrides, silicon oxynitrides, aluminum oxides, titanium oxides, titanium nitride, titanium oxynitride, tin oxides, zirconium oxides, zeolites or combinations thereof. Porous silica is an especially desirable inorganic detection layer material due to its robustness and compatibility with wet etching treatments.

Porous silicas may be prepared, for example, using a sol-gel processing route and made with or without an organic template. Exemplary organic templates include surfactants, e.g., anionic or nonionic surfactants such as alkyltrimethylammonium salts, poly(ethyleneoxide-co-propylene oxide) block copolymers and other surfactants or polymers that will be apparent to persons having ordinary skill in the art. The sol-gel mixture may be converted to a silicate and the organic template may be removed to leave a network of micropores within the silica. Representative porous silica materials are described in Ogawa et al., *Chem. Commun.* pp. 1149-1150 (1996), in Kresge et al., *Nature*, Vol. 359, pp. 710-712 (1992), in Jia et al., *Chemistry Letters*, Vol. 33(2), pp. 202-203 (2004) and in U.S. Pat. No. 5,858,457 (Brinker et al.). A variety of organic molecules may also be employed as organic templates. For example, sugars such as glucose and mannose may be used as organic templates to generate porous silicates, see Wei et al, *Adv. Mater.* 1998, Vol. 10, p. 313 (1998). Organo-substituted siloxanes or -organo-bis-siloxanes may be included in the sol-gel composition to render the micropores more hydrophobic and limit sorption of water vapor. Plasma chemical vapor deposition may also be employed to generate porous inorganic detection materials. This methodology generally involves forming an analyte detection layer by forming a plasma from gaseous precursors, depositing the plasma on a substrate to form an amorphous random covalent network layer, and then heating the amorphous covalent network layer to form a microporous amorphous random covalent network layer. Examples of such materials are described in U.S. Pat. No. 6,312,793 (Grill et al.) and U.S. Patent Publication No. 2007/0141580A1 (Moses et al.).

Representative organic detection layer materials include polymers, copolymers (including block copolymers) and mixtures thereof prepared or preparable from classes of monomers including hydrophobic acrylates and methacrylates, difunctional monomers, vinyl monomers, hydrocarbon monomers (olefins), silane monomers, fluorinated monomers, hydroxylated monomers, acrylamides, anhydrides, aldehyde-functionalized monomers, amine- or amine salt-functionalized monomers, acid-functionalized monomers, epoxide-functionalized monomers and mixtures or combinations thereof. The U.S. Patent Application Publication No. US 2004/0184948 contains an extensive list of such monomers and reference is made thereto for further details. The above-mentioned polymers having intrinsic microporosity (PIMs) provide particularly desirable detection media. PIMs typically are non-network polymers that form microporous solids. Due to their typically highly rigid and contorted molecular structures, PIMs are unable to fill space efficiently, thus providing the disclosed microporous structure. Suitable PIMs include, but are not limited to, polymers disclosed in "Polymers of intrinsic microporosity (PIMs): robust, solution-processable, organic microporous materials," Budd et al., *Chem. Commun.,* 2004, pp. 230-231. Additional PIMs are disclosed in Budd et al., *J. Mater. Chem.*, 2005, 15, pp. 1977-1986, in McKeown et al., *Chem. Eur. J.* 2005, 11, No. 9, 2610-2620 and in Published PCT application No. WO 2005/012397 A2 (McKeown et al.).

One or more polymers within an organic detection layer may be at least partially crosslinked. Crosslinking may be desirable in some embodiments because it can increase mechanical stability and sensitivity to certain analytes. Crosslinking can be achieved by incorporating one or more multifunctional monomers into the detection layer, by subjecting the detection layer to, e.g., electron beam or gamma ray treatment, by adding or forming coordination compounds or ionic compounds in the detection layer, or by forming hydrogen bonds in the detection layer. In one exemplary embodiment, crosslinking is carried out in the presence of a porogen which may be subsequently extracted from the crosslinked system to yield a porous detection layer. Suitable porogens include, but are not limited to, inert organic molecules, such as normal alkanes (e.g., decane) or aromatics (e.g., benzene or toluene). Other crosslinked polymers include the above-mentioned highly crosslinked styrenic polymers.

If desired, the detection layer material may be treated to modify its surface properties or adsorption characteristics. A variety of such treatments may be employed, e.g., by exposing the micropores of an inorganic detection layer to a suitable organosilane compound. The detection medium may also or instead be treated with a suitable adhesion promoting material (e.g., a tie layer made of titanium or another suitable metal) to promote adhesion between the partially reflective or reflective layer and the detection layer. Such treatments may also be applied to the partially reflective or reflective layers to promote adhesion to the detection medium.

For many applications, the detection layer material desirably is hydrophobic. This will reduce the chance that water vapor (or liquid water) will cause a change in the detection layer optical thickness and interfere with the detection of an analyte, for example, the detection of organic solvent vapors. The detection layer may be made from a single layer or from two or more sublayers.

The sensing element may also be a patterned chemical sensor such as those described in Ser. No. 12/604,565 "Patterned Chemical Sensor Having Inert Occluding Layer" filed Oct. 23, 2009. These patterned sensors comprise a film that includes a film body that comprises a detection layer and an occluding layer that is bound to the film body and occludes a portion of the detection layer. The detection layer is responsive to an organic chemical, i.e. the detection layer changes color upon exposure to the organic chemical. The occluding layer precludes the chemical to be detected from accessing the occluded area and causing the color change. The net effect of this arrangement is that in a single film body, upon exposure to an organic chemical, the "old" color (that is to say the initial color state) of the detection layer and the "new" color (that is to say the changed color state of the detection layer) are present side by side, permitting the user to readily determine if a change has occurred.

A variety of devices may be used as readers to observe the sensing element for changes. The choice of reading device can depend upon a variety of factors such as, for example, ease of use of the monitor, expense of the monitor, portability of the monitor, robustness of the monitor, the need for the monitor to provide multiple signals (such as visual and auditory signals), and the like.

In some embodiments, the reader for the sensing element is the human eye, and monitoring of sensing element is done by visual observation to observe a visible change in the sensing element, such as a color change. In this way a user, or a group of users can easily monitor the service life remaining in their respirator masks or filter cartridges within their respirator masks. Visual monitoring is a very simple and inexpensive method of monitoring, requiring no additional equipment, power sources, or delicate components.

In other embodiments, an electronic optical reader may be used to monitor the sensing element to detect changes. Advantages of using an electronic system include higher accuracy of reading the sensing element and the monitor can provide multiple signals. For example, when the electronic reader detects a change in the sensing element, a light can flash as a warning to users in the environment, an audible signal can be generated such as a buzzer or claxon, or an electronic signal can be sent to electronic receiver carried by users in the environment.

Examples of suitable electronic optical reader systems are described, for example in Ser. No. 61/320,427 "Filter Systems Including Optical Analyte Sensors And Optical Readers" filed Apr. 2, 2010. Typically, suitable optical readers include at least one light source and at least one detector. The optical reader can be configured such that at least a portion of light emitted by at least one light source is reflected from the sensing element and captured by the at least one detector.

The one or more light sources may include any of a variety of light sources. For example, light-emitting diodes (LEDs) can be used. In certain embodiments, one or more light sources may include one or more relatively broadband light sources (e.g., white light sources). In other embodiments, light sources may include one or more narrowband light sources (e.g., LEDs) that emit light in a particular (e.g., relatively narrow) wavelength range with a peak at a particular wavelength within that range. In various embodiments, such narrowband light sources may be characterized by a half-power bandwidth of at most about 50 nm, at most about 40 nm, or at most about 25 nm. Exemplary LEDs that may be used include those available from Optek, Carrollton, Tex., under the designation OVLBx4C7, and surface mount LEDs such as the LS T676, LA T676, LO T676, LY T676 series from Osram.

Suitable detectors for use in the electronic optical reader may include any of a variety of devices capable of measuring the amount of light incident thereon, including for example photodetectors such as a photomultiplier tube, a photovoltaic cell, a photodiode, a phototransistor, a charge coupled device, and the like. A suitable detector may serve to provide a signal (e.g., voltage, current, etc.) that is related to the amount of light detected (e.g., to the intensity or strength of the reflected light received from the sensing element) and that can be further processed. In some embodiments one or more detectors may detect light of a particular (e.g., relatively narrow) wavelength range. In other embodiments, one or more detectors may include a broadband detector that can detect light over relatively wide range of wavelengths. In various embodiments, such broadband detectors may be able to detect light over a wavelength range of at least about 150 nm wide, 250 nm wide, or 500 nm wide. Exemplary detectors that can be used include photodiodes available from OSRAM, Regensburg, Germany, under the designation SFH 2430.

Multiple light sources may be used as a part of the optical reader. For example, first and second light sources each may be characterized by first and second spectral (or wavelength) ranges and first and second peak wavelengths. The first spectral range may be different from the first spectral range and the first and second light sources can emit light with different peak wavelengths. In such a design, the different light sources may be mounted next to a common detector.

The first and second light sources may be chosen such that their spectra are characterized by different wavelength ranges A and B and different peak wavelengths. In such embodiments, a single (e.g., broadband) photodetector may be used as the detector. The monitoring of light reflected from the optical analyte sensor in multiple wavelength ranges may provide significant advantages. The various details and principles of such detection are set forth, for example, in a commonly owned U.S. Provisional Application No. 61/164,496 (Hulteen et al.).

Alternatively, the optical reader may include two light sources and two detectors. Such an optical reader also can be configured such that at least a portion of light emitted by at least one light source is reflected from the sensing element and captured by the detectors. The light sources each may emit light in a different wavelength range with a different peak wavelength than that emitted by the other light source. Each light source can be used in combination with a photodetector designed to detect light in the particular wavelength range emitted by the corresponding light source.

The electronic optical reader may contain further components. For example, the electronic optical reader may further include a battery, an alerting device, such as one or more light sources or a monitor screen, and an actuator. A user may trigger the actuator to initiate the interrogation of an sensing element by the optical reader. The optical reader may be connected to other electronic devices, such as a computer by a serial interface. Thus, the optical reader may communicate various information to, for example, a display.

A wide variety of devices may be used as the fluid delivery device as long as they can reliably control the flow rate through the monitoring device. Among the useful fluid delivery devices are fans and pumps. The fan or pump typically is electrically powered, but in some embodiments a hand-powered device such as a hand-powered pump may be suitable.

A wide variety of suitable fans and pumps are commercially available. One suitable class of pumps are micro diaphragm gas sampling pumps such as those commercially available from KNF Neuberger, Inc., Trenton, N.J. under the trade names NMP 05 S (with a brush type motor), NMP 09 M (with an ironless core motor), and NMP 015 B (with a brushless DC motor). Other suitable fans and pumps are known in the air purification arts.

The device may further comprise a receptacle. The receptacle may contain the demand substance or it may contain the demand substance and at least one sensing element. A wide variety of receptacles are possible. The receptacle may be, for example, a tube, a cartridge, a ox, or a disk depending upon the overall shape and design of the device.

In some embodiments, the receptacle is a tube. The tube may be made of glass or plastic and if the sensing element is included in the receptacle it may be desirable that the tube be transparent.

The entire monitoring device may be housed within a case. The case can hold the receptacle that contains the demand substance. The receptacle may also contain at least one sensing element, or there may be sensing elements in fluid communication with the receptacle within the case. The case can also hold the fluid delivery device. As discussed above, the fluid delivery device may be a fan or pump and may be electrically powered by a source such as a battery or it may be hand-powered. The case can also contain the reader for the sensing element. In some embodiments, where the sensing element is read by the human eye, the reader may be a window or other orifice through which the sensing element can be monitored. The window or other orifice may be an opening or it may be covered by a transparent cover. In other embodiments where the sensing element is monitored electronically, the reader may interact with, for example, a display screen or other electronic data delivery means.

Several embodiments of the monitors of this disclosure are presented in the figures. FIG. 1 shows a perspective view of an exemplary portable monitor of this disclosure. In FIG. 1, portable monitor 100 contains fluid inlet 110, reader window 120 and control buttons 130. Fluid inlet 110 may be a simple orifice or it may be an orifice with a cover (not shown), the cover being or containing a screen or a plurality of smaller orifices. The cover, if present, may be detachable. In this relatively simple portable monitor, the gas to be monitored enters fluid inlet 110, and a user may monitor the sensing element (not shown) by observing the sensing element through reader window 120. Note that the location and size of the reader window 120 may be varied in different embodiments to permit easy viewing of the sensing element. The reader window 120 may simply be an aperture or it may have a transparent cover such as glass or a polymeric material (for example polycarbonate or polyacrylate). The control buttons 130 control the fluid delivery device within the portable monitor (not shown). The fluid delivery device may be a fan or a pump, typically it is a pump. While two control buttons are shown in FIG. 1, fewer or more control buttons may be present as well as control switches or even dials. In the embodiment shown in FIG. 1, the two control buttons can turn the fluid delivery device on and off and/or control the speed with which the fluid passes through the portable monitor.

Figure 2:
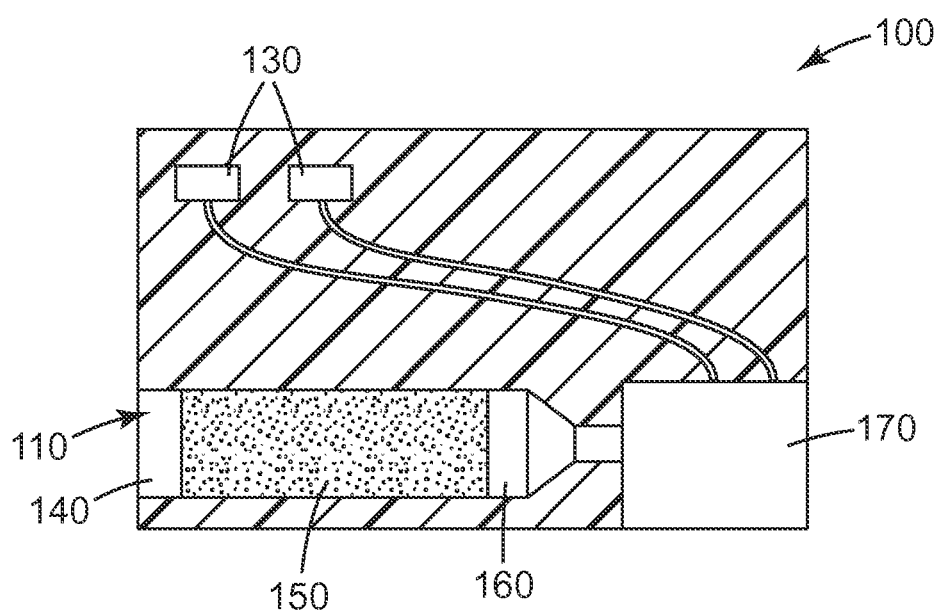
FIG. 2 shows a cut away view of an embodiment of the portable monitor of FIG. 1.

FIG. 2 is a cut away view of the portable monitor of FIG. 1, cut along the plane 2 shown in FIG. 1. In this embodiment, gases that pass into fluid inlet 110 pass into receptacle 140 containing demand substance 150 and sensing element 160. The gases are pulled through the receptacle by fluid delivery device 170, which is this embodiment is a pump, and is controlled by control buttons 130.

Figure 3:
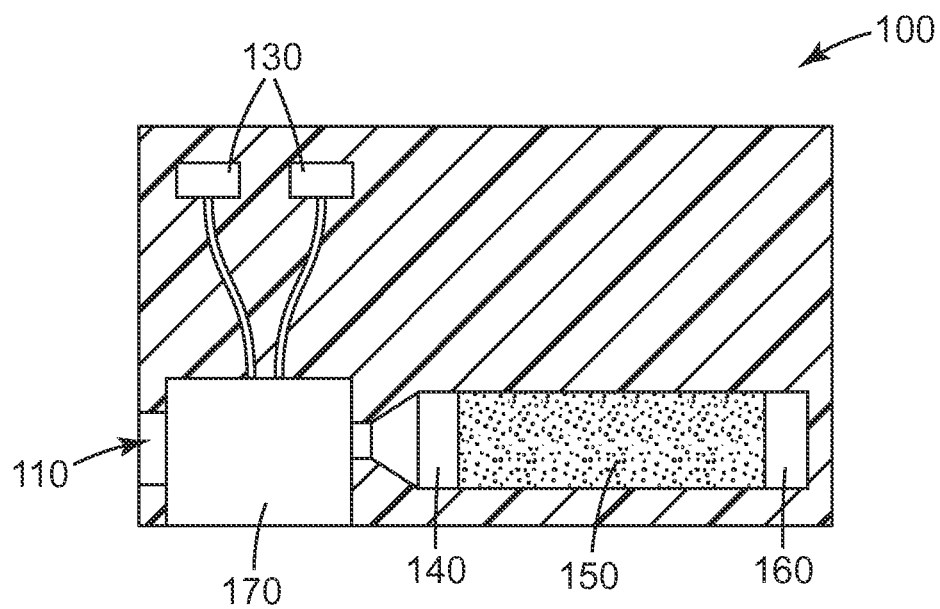
FIG. 3 shows a cut away view of an alternative embodiment of the portable monitor of FIG. 1.

FIG. 3 is a cut away view of an alternative embodiment of the portable monitor of FIG. 1, cut along the plane 2 shown in FIG. 1. In this embodiment, gases that pass into fluid inlet 110 pass into fluid delivery device 170, enter receptacle 140 containing demand substance 150 and sensing element 160. In this embodiment, the gases are pushed through the receptacle by fluid delivery device 170, which is this embodiment is a pump, and is controlled by control buttons 130.

Figure 4:
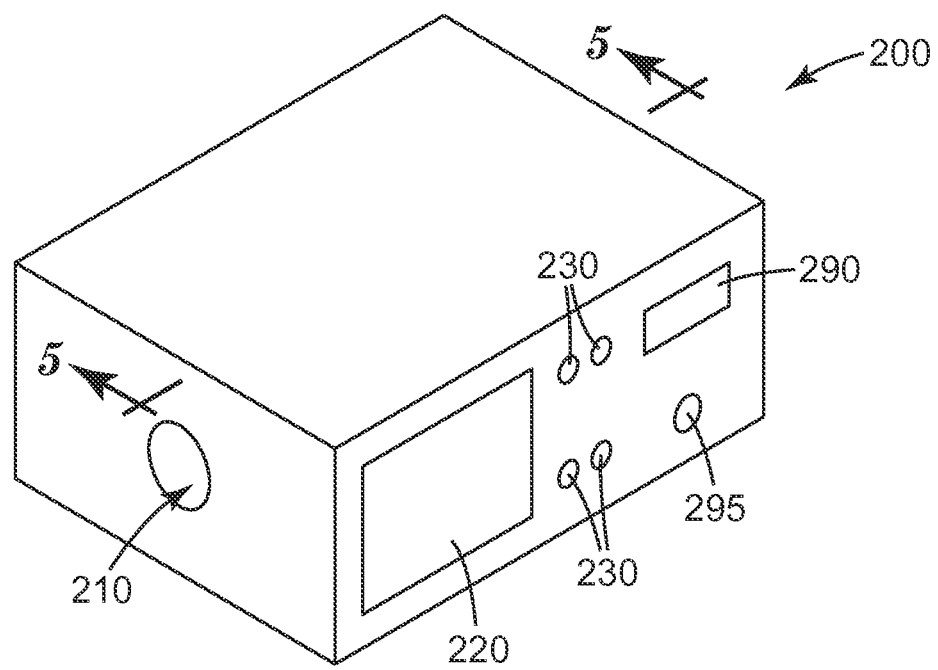
FIG. 4 shows a perspective view of an alternative portable monitor of this disclosure.

FIG. 4 shows a perspective view of a different exemplary portable monitor of this disclosure. In FIG. 4, portable monitor 200 contains fluid inlet 210, reader screen 220, control buttons 230, speaker 290, and light 295. In this more complex portable monitor the gas to be monitored enters fluid inlet 110, and a user may monitor the sensing element (not shown) by observing the reader screen 220, which is an electronic screen that may contain a variety of messages and information. For example, the reader screen can convey information such as: the status of the monitor (on or off); the time it has been in service; the time left before end of service life; etc. The control buttons 230 can control the fluid delivery device as in the portable monitor 100 as well as controlling the functions of the reader screen 220. The speaker 290 and light 295 are optional additional warning devices that can be employed with the portable monitor. The speaker can broadcast an audible signal or message to alert a user of change of status of the portable monitor or that the end of service life has been reached or is approaching. Similarly the light can turn on or begin flashing as an additional indicator to the user that the portable monitor should be checked.

Figure 5:
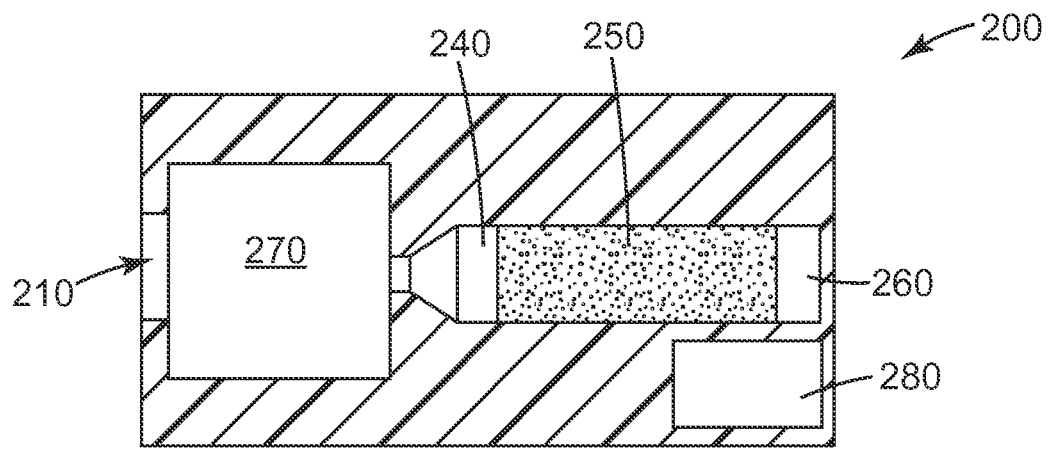
FIG. 5 shows a cut away view of an embodiment of the portable monitor of FIG. 4.

FIG. 5 is a cut away view of one embodiment of the portable monitor of FIG. 4, cut along the plane 5 shown in FIG. 4. Gases enter the portable monitor through gas inlet 210, enter fluid delivery device (pump) 270 and enter receptacle 240 containing demand substance 250 and sensing element 260. Sensing element 260 can be monitored by reader 280. Reader 280 is an electronic reader to detect changes in sensing element 260. Reader 280 sends output to the reader screen (not shown but shown as element 220 in FIG. 4).

Figure 6:
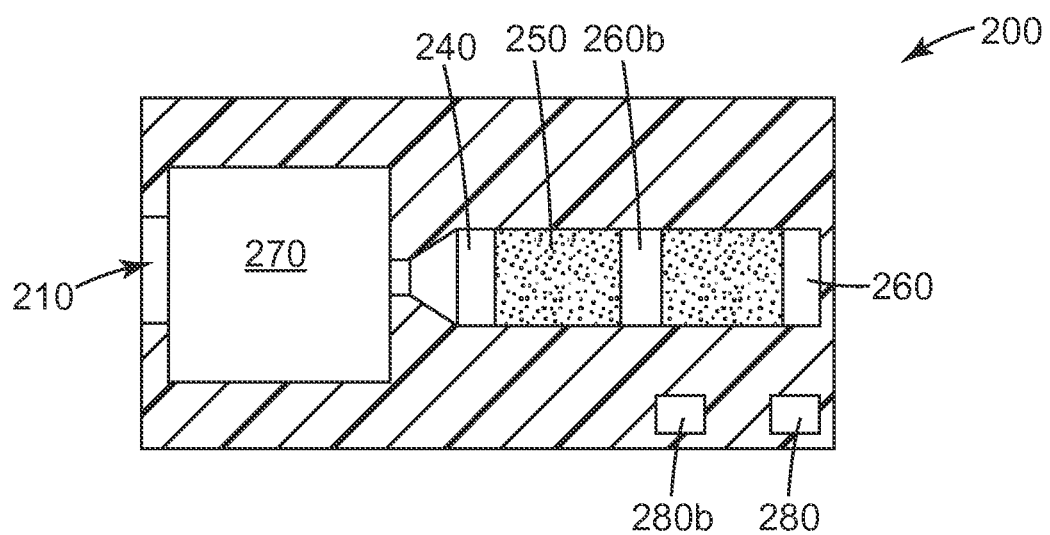
FIG. 6 shows a cut away view of an alternative embodiment of the portable monitor of FIG. 4.

FIG. 6 is a cut away view of an alternative embodiment of the portable monitor of FIG. 4, cut along the plane 5 shown in FIG. 4. The above listed elements are all present, as well as additional sensing element 260b and additional reader 280b. The additional sensing element and reader can give the portable monitor the ability to sense additional organic vapors, provide additional sensing output or both. Sensing element 260b may be the same, similar or different from sensing element 260. Similarly, depending upon the nature of sensing element 260b, reader 280b may be same, similar or different from reader 280.

Figure 7:
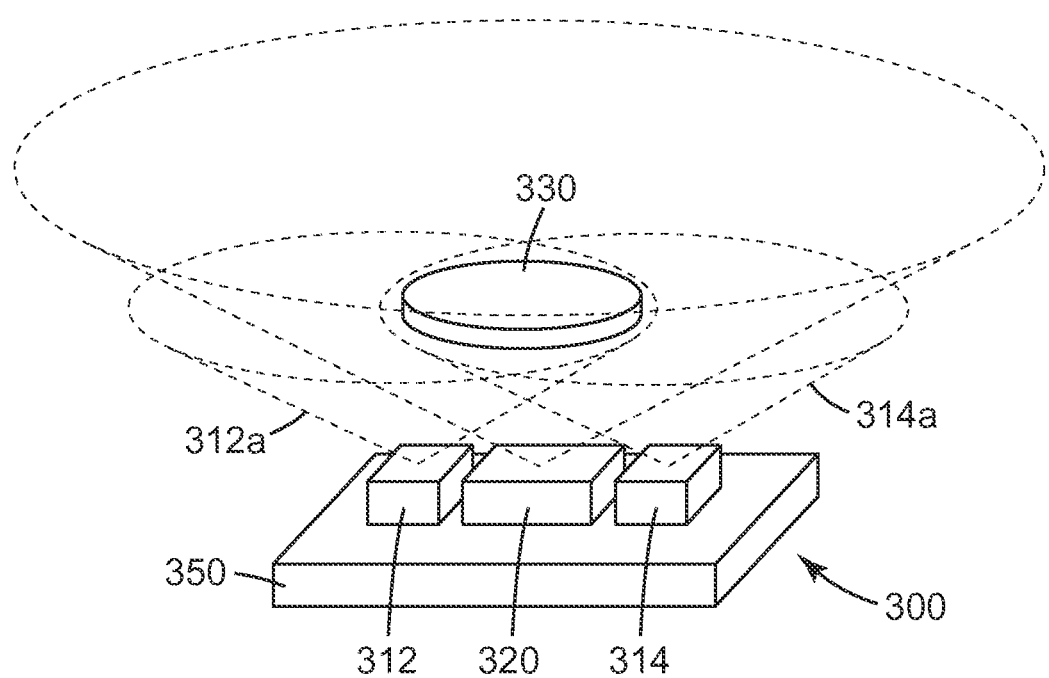
FIG. 7 shows an exemplary optical reader according to the present disclosure.

FIG. 7 shows an exemplary optical reader 300 suitable for use with the monitors of the present disclosure. The optical reader 300 includes at least one light source (here, 312 and 314) and at least one detector 320. One or more light sources (e.g., 312 and 314) and one or more detectors 320 can be mounted on the same support 350. The optical reader 300 can be configured to be attached to the case of the monitor according to the present disclosure. The sensing element 330, is shown as a disk but may be in any suitable shape and may be included in the receptacle (not shown) or be located such that the exit stream from the receptacle impinges upon the sensing element 330. At least a portion of light 312a, 314a emitted by at least one light source 312, 314 is reflected from the sensing element 330 and captured by the at least one detector 320.

EXAMPLES

These examples are merely for illustrative purposes only and are not meant to be limiting on the scope of the appended claims.

Example 1

Test monitor tubes were prepared to predict the service life for the 6001 series OV filter cartridges commercially available from 3M Company, St. Paul, Minn.

Test Sample Preparation:

A series of test monitor tubes containing demand substance were prepared in glass tubes. The demand substance used was Kuraray GG 12×20 activated carbon (the same carbon used in the 6001 series OV cartridges). The demand substance loaded portion of the tube measured 110 millimeters in length and 9.4 millimeters in diameter.

Organic Vapor Testing:

For the organic vapor testing, nitrogen that is free of organic vapors was passed through the test monitor tube first to establish a flow. The organic vapor streams listed in Table 1 were then passed through the test monitor tube and monitored to 50% breakthrough using a MIRAN Sapphire XL infrared spectrometer. The breakthrough times are shown in Table 1. Organic vapor streams were generated by flowing nitrogen gas through a cooled impinger containing the solvent of interest; the streams were subsequently diluted with additional nitrogen (controlled with mass flow controllers) and monitored using a MIRAN Sapphire XL infrared spectrometer. The spectrometer was first used to determine correct ppm delivery of the input stream, and was then connected to the tube outlet to track exit concentration.

Correlation Calculations:

A mathematical model has been established by Gerry Wood (see: *Am. Ind. Hyg. Assn. J.* 55(1): 11-15, 1994) that allows one to calculate an anticipated cartridge service life time for an activated carbon filter bed as a function of vapor identity and concentration.

The model describes time to breakthrough, $t_b$, as:

$$t_b = (W_e W/C_o Q) - (1000\, W_e \rho_\beta / k_v C_o) \ln [(C_0 - C_x)/C_x]$$

where:
$C_x$ = exit concentration (g/L)
$C_o$ = inlet concentration (g/L)
$Q$ = volumetric flow rate (L/min)
$W$ = weight of activated carbon (g)
$\rho_\beta$ = packed density of the carbon bed (g/cc)
$W_e$ = equilibrium adsorption capacity (g/g of carbon)
$K_v$ = adsorption rate coefficient (1/min)

The 50% breakthrough point is defined as the point at which $C_o = 2C_x$. At the 50% breakthrough point, the ln $[(C_0-C_x)/C_x]$ term goes to zero, so that $t_b = (W_e W/C_o Q)$. The predicted breakthrough time of 3M 6001 filter cartridge can be calculated for a given organic vapor concentration and flow rate. These calculated values are presented in Table 2.

The experimental breakthrough times for the sample cartridges were correlated to give predicted 50% breakthrough times for the 3M 6001 filter cartridge by multiplying the carbon tube breakthrough time by $(W_{cartridge} Q_{tube} / W_{tube} Q_{cartridge})$. The predicted breakthrough times for the filter cartridge calculated from the experimental breakthrough times of the test monitor tubes are also shown in Table 2. The Percent Difference between the predicted breakthrough times for the filter cartridge calculated from the experimental breakthrough times of the test monitor tubes and the calculated filter cartridge breakthrough times were calculated from the equation is also shown in Table 2:

% Difference=(Predicted−Calculated)/Calculated× 100%.

Residence Time Correlation Calculations:

Calculations were carried out to determine the residence time for the test monitor tube and the 3M 6001 series OV filter cartridge. Using the dimensions of the test monitor tube and the experimental flow rate of 3.2 L/min the residence time was calculated to be 0.14 seconds. Assuming a cartridge breathing rate of 32 L/min and using the 3M 6001 cartridge dimensions the residence time was determined as 0.19 seconds. The residence times allow one to predict 50% breakthrough time for the 6001 cartridge from the measured 50% breakthrough time of the test monitor tube by multiplying the 50% breakthrough time on the test monitor tube by the ratio of residence time cartridge over residence time tube as shown in Table 3.

TABLE 1

| Example | Organic Vapor Identity | Tube Carbon Weight (grams) | Vapor Flow Rate (L/min) | Organic Vapor Concentration (ppm) | 50% Breakthrough Time (min) |
|---|---|---|---|---|---|
| 1A | Toluene | 3.23 | 3.2 | 788 | 158 |
| 1B | Toluene | 3.31 | 3.2 | 871 | 145 |
| 1C | Heptane | 3.22 | 3.2 | 952 | 80 |
| 1D | Styrene | 3.24 | 3.2 | 818 | 178 |
| 1E | 1-Butanol | 3.22 | 3.2 | 746 | 201 |

TABLE 2

| Example | 50% Breakthrough Time of Tube Measured (min) | Predicted 6001 Cartridge 50% Breakthrough Time From Experimental Data (min) | Calculated 6001 Cartridge 50% Breakthrough Time (min) | Difference Between Predicted and Calculated (%) |
|---|---|---|---|---|
| 1A | 158 | 225.0 | 209.0 | 7.66 |
| 1B | 145 | 206.5 | 191.6 | 7.78 |
| 1C | 80 | 113.9 | 127.0 | 10.29 |
| 1D | 178 | 253.5 | 213.5 | 18.73 |
| 1E | 201 | 286.3 | 269.2 | 6.34 |

TABLE 3

| Example | Vapor Flow Rate (L/min) | 50% Breakthrough Time Carbon Tube Measured (min) | Wood Model Calculations Breakthrough Time at 50% for 6001 cartridge, 32 L/min (min) | Predicted 50% Breakthrough Time for 6001 Cartridge from Residence Time Ratio (min) |
|---|---|---|---|---|
| 1A | 3.2 | 158 | 209 | 209 |
| 1B | 3.2 | 145 | 192 | 192 |
| 1C | 3.2 | 80 | 127 | 106 |
| 1D | 3.2 | 178 | 214 | 235 |
| 1E | 3.2 | 201 | 269 | 266 |

Example 2

Test monitor tubes were prepared to predict the service life for the 6001 series OV filter cartridges commercially available from 3M Company, St. Paul, Minn.

Preparation of Sensing Film:

The sensor film was prepared by first coating a sample of Melinex ST 504 PET (polyethylene terephthalate) film with a thickness of 127 micrometers (5 mils) with Au/Pd (35 mAmps, 20 seconds) using a benchtop sputter coater. An intrinsically microporous polymer (PIM) was prepared using methods described previously in the literature (Chem. Comm., 2004, pp. 230-231). The polymer was dissolved to 4% conc. by mass in tetrahydropyran (THP) and spincoated onto the Au/Pd layer at 1000 rpm. A silver nanoparticle ink (stock solution obtained from Cabot Labs, batch 457010, 20.1% wt) was diluted (0.5 grams of the obtained stock solution plus 1 milliliter of ethanol) and spincoated at 1000 rpm onto the PIM layer to complete the sensor stack. The multilayered film was then heated at 125 degrees Celsius for 2 hrs. prior to use.

Test Sample Preparation:

A test monitor tube containing a sensing film was prepared to mimic the 6001 series OV filter cartridges commercially available from 3M Company, St. Paul, Minn. The sensor film was placed inside a tube as described above in Example 1, prior to filling and pressed down to conform as tightly to the glass surface as possible. Kuraray GG 12×20 activated carbon (the same carbon used in the 6001 series OV cartridges) was then loaded into the tube. The sensor film and fiber probe were positioned 88 millimeters (or 80% of the full 110 millimeter length of the tube, giving 20% remaining carbon capacity) from the entry point of the tube.

Organic Vapor Testing:

Organic Vapor testing with toluene was carried out (854 ppm, 3.2 L/min flow) as described above in Example 1, except that an Ocean Optics fiber optic spectrometer was used to monitor the sensor film while the MIRAN IR spectrometer analyzed the exit gas coming from the tube end. The IR-measured 50% breakthrough time (at the end of the tube) as well as the measured 50% breakthrough time from the Sensor Film Response (with 20% of carbon remaining) are shown in Table 4.

Correlation Calculations:

Calculations were carried out as described above to give the Calculated Breakthrough Time with 20% of Carbon Remaining for the filter cartridge and the Predicted Breakthrough Time with 20% of Carbon Remaining from the Sensor Film Experimental Data. These values are shown in Table 4 along with % Difference, calculated as described above for Example 1.

TABLE 4

| Measured 50% Breakthrough Time of Tube End of Tube (min) | Measured 50% Breakthrough Time of Tube Sensor Film with 20% of Carbon Remaining (min) | Predicted 6001 Cartridge 50% Breakthrough Time From Experimental Data with 20% of Carbon Remaining (min) | Calculated 6001 Cartridge 50% Breakthrough Time with 20% of Carbon Remaining (min) | Difference Between Predicted and Calculated (%) |
|---|---|---|---|---|
| 152 | 118 | 168 | 154 | 9.1 |

What is claimed is:

1. A method of correlating a monitoring device to the service life of a filter cartridge comprising:
   providing a monitoring device; and
   calibrating the monitoring device to correspond to the service life of a filter cartridge,
   wherein the monitoring device comprises:
     a demand substance capable of absorbing an organic vapor within a receptacle;
     a sensing element with a detection point;
     a reader for the sensing element; and
     a fluid delivery device, the fluid delivery device comprising fluid delivery parameters, wherein the fluid delivery parameters and the detection point of the sensing element are correlated to the service life of a filter cartridge, and
   wherein calibrating the monitoring device to correspond to the service life of a filter cartridge comprises:
     determining a residence time for the filter cartridge;
     determining a residence time for the monitoring device;
     determining the ratio of the residence time of the monitoring device to the residence time of the filter cartridge; and
     utilizing the ratio to correlate the response of the sensor within the monitoring device to the service life of the filter cartridge.

2. The method of claim 1, wherein the response of the sensor within the monitoring device is correlated to the service life of the filter cartridge by control of the fluid delivery parameters of the fluid delivery device, wherein the fluid delivery parameters comprise: the flow rate, the demand substance mass, the receptacle cross sectional area, the receptacle volume, the receptacle length, and the demand substance packing density of the monitoring device.

3. The method of claim 2, wherein the demand substance and the demand substance packing density for the monitoring device and the filter cartridge are the same.

4. The method of claim 3, wherein the demand substance for the monitoring device and the filter cartridge comprises activated carbon, treated activated carbon, alumina, silica gel, hopcalite, molecular sieves, metal-organic frameworks, or a combination thereof.

5. The method of claim 2, wherein the flow rate for the monitoring device is different from the flow rate for the filter cartridge.

6. The method of claim 1, wherein the fluid delivery device controls the flow rate to make the ratio of the face velocity of the monitoring device to the face velocity of the filter cartridge equal 1:1.

7. The method of claim 1, wherein the fluid delivery device controls the flow rate to make the ratio of the residence time of the monitoring device to the residence time of the filter cartridge is less than 1:1.

8. The method of claim 1, wherein the detection point of the sensing element comprises an optical change.

9. The method of claim 8, wherein the optical change comprises a change in color.

10. The method of claim 1, wherein the reader for the sensing element comprises the human eye or an optical detector.

11. The method of claim 1, wherein the demand substance is a layered film.

12. The method of claim 1, wherein the receptacle contains the demand substance and at least one sensing element.

13. The method of claim 1, wherein the receptacle comprises a tube, a cartridge or a disk.

14. The method of claim 1, wherein the monitoring device further comprises additional sensing elements.

15. The method of claim 1, wherein the fluid delivery device comprises a pump or fan.

16. The method of claim 3, wherein the service life of the filter cartridge is described by the equation:

$$t_{SL} = t_b(W_{cartridge} Q_{monitor} / W_{monitor} Q_{cartridge})$$

wherein $t_{SL}$ is the service life time of the filter cartridge;

$t_b$ is the service life time of the monitor;

$W_{cartridge}$ is the weight of demand substance in the cartridge;

$Q_{monitor}$ is the flow rate in the monitor;

W monitor is the weight of demand substance in the monitor;

$Q_{cartridge}$ is the flow rate in the cartridge.

17. The method of claim 16, wherein $t_b$ is the same as the detection point of the sensing element.

18. The method of claim 16, wherein $W_{cartridge} Q_{monitor} = W_{monitor} Q_{cartridge}$.

19. The method of claim 17, wherein the detection point is less than $t_b$.

20. The method of claim 1, wherein the sensing element is a layered film.

* * * * *